United States Patent [19]

Saitoh et al.

[11] Patent Number: 4,792,545
[45] Date of Patent: Dec. 20, 1988

[54] BOHOLMYCIN ANTIBIOTIC

[75] Inventors: Kyoichiro Saitoh, Zushi; Mitsuaki Tsunakawa, Tokyo; Masataka Konishi, Kawasaki; Takeo Miyaki, Yokohama, all of Japan

[73] Assignee: Bristol-Myers Company, New York, N.Y.

[21] Appl. No.: 817,212

[22] Filed: Jan. 8, 1986

[51] Int. Cl.$^4$ .................. A61K 31/71; C07H 15/20
[52] U.S. Cl. .................. 514/35; 536/16.8; 536/17.2; 536/17.9; 435/82; 435/83
[58] Field of Search .............. 536/16.8, 13.2, 13.3, 536/17.2, 17.9; 514/41, 35

[56] References Cited

U.S. PATENT DOCUMENTS 4,468,386  8/1984  Hanada et al. .............. 536/16.8
4,656,160  4/1987  Takaya et al. .............. 536/16.8

OTHER PUBLICATIONS

*J. Antibiotics* 29(11), Sorbistin, A New Aminoglycoside Antibiotic Complex of Bacterial Origin, Hiroshi Tsukiura et al., pp. 1137–1146.

*Primary Examiner*—Johnnie R. Brown
*Assistant Examiner*—Elli Peselev
*Attorney, Agent, or Firm*—David Morse

[57] ABSTRACT

Boholmycin antibiotic is prepared by fermentation of *Streptomyces hygroscopicus* H617-25 (ATCC No. 53240) in a nutrient medium preferably comprising glycerol, bacto-liver, cornsteep liquor, ammonium sulfate, sodium chloride and calcium carbonate. The antibiotic and pharmaceutically acceptable salts and hydrates thereof and compositions containing these are effective against Gram-positive, Gram-negative and acid-fast bacteria and against bacterial strains which are resistant to previously known aminoglycoside antibiotics and are useful to treat bacterial infections in mammals.

3 Claims, 3 Drawing Sheets

BOHOLMYCIN ANTIBIOTIC

TECHNICAL FIELD

This invention is directed to novel antibiotics, to a novel microorganism for producing the antibiotics, to a method of producing the antibiotic utilizing the microorganism, to compositions containing the antibiotics and to a method of treating bacterial infections with the antibiotics.

BACKGROUND OF THE INVENTION

Previous aminoglycoside antibiotic complexes have been reported in literature such as in *J. Antibiotics* 29:1137-1146 (1976) which discusses sorbistin. These aminoglycosides possess specific antibacterial activity.

It is an object of the instant invention to produce an aminoglycoside antibiotic having broad spectrum activity. Broad spectrum activity is used herein to mean possessing antibacterial activity to Gram-positive, Gram-negative and acid-fast bacteria. It is a further object of the instant invention to provide an aminoglycoside antibiotic complex which possesses antibacterial aciivity against bacterial strains which are resistant to previously known aminoglycoside antibiotics.

SUMMARY OF THE INVENTION

The novel antibiotics herein are boholmycin which has been determined to have the structural formula:

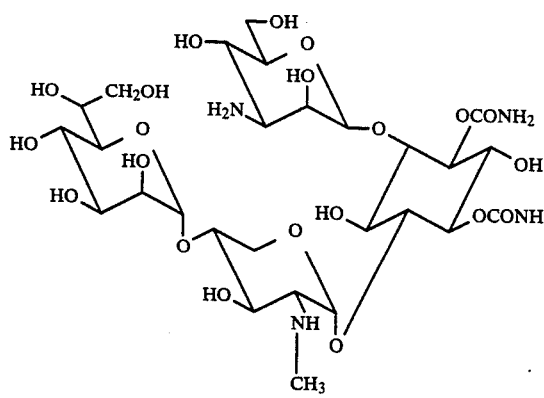

and its non toxic pharmaceutically acceptable salts and hydrates (including hydrated salts). Boholmycin is a novel type of aminoglycoside composed of bonded heptose, two aminosugars and a substituted scyllo-inositol.

The boholmycin antibioties are readily produced by culturing a novel microorganism *Streptomyces hygroscopicus* strain H617-25 (ATCC No. 53240) under aerobic conditions at a temperature ranging from 15° C. to 45° C. in nutrient media and separating and recovering the antibiotic. The acid addition salts and hydrates of boholmycin are readily made up by methods known in the art.

The antibiotics herein and compositions containing them together with a suitable pharmaceutically acceptable carrier are effective against a variety of microorganisms and are administered to mammals for treatment and control of antibacterial infections in an amount suitable for such treatment, i.e. in a therapeutically effective amount.

DETAILED DESCRIPTION OF THE INVENTION

Boholmycin and its pharmaceutically acceptable salts are water-soluble, weakly basic antibiotics. They are freely soluble in water, slightly soluble in methanol and ethanol but practically insoluble in other organic solvents. Boholmycin gives a positive reaction in ninhydrin and anthrone tests, but is negative to Tollen's and Sakaguchi reagents. The antibiotic is reasonably stable in neutral and acidic solution but unstable in alkaline solution.

Figure 1:
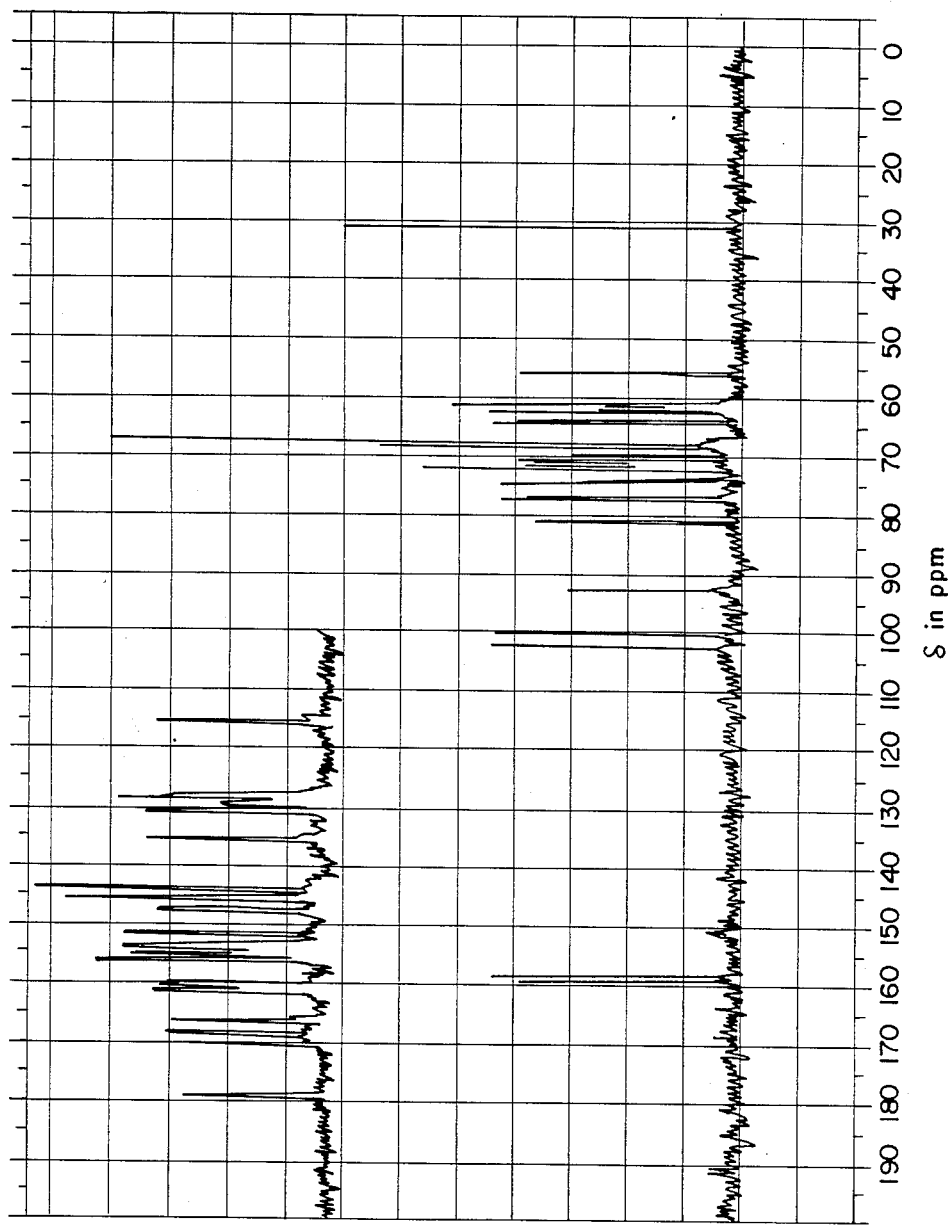
FIG. 1—$^{13}$C-NMR spectrum of boholmycin hydrochloride at 20 MHz, in $D_2O$ at PD 5.0.
Figure 2:
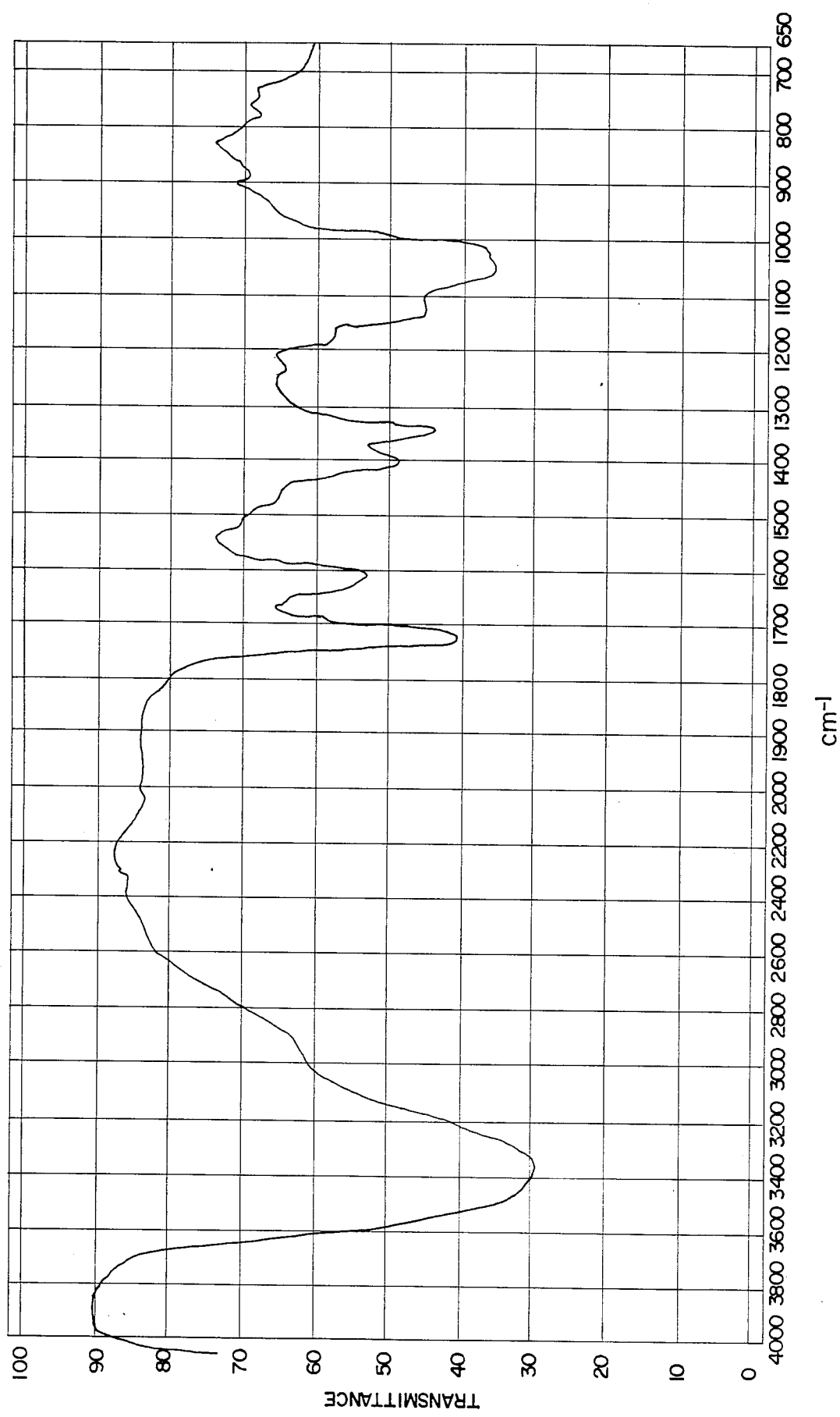
FIG. 2—Infrared absorption spectrum of boholmycin hydrochloride in KBr.
Figure 3:
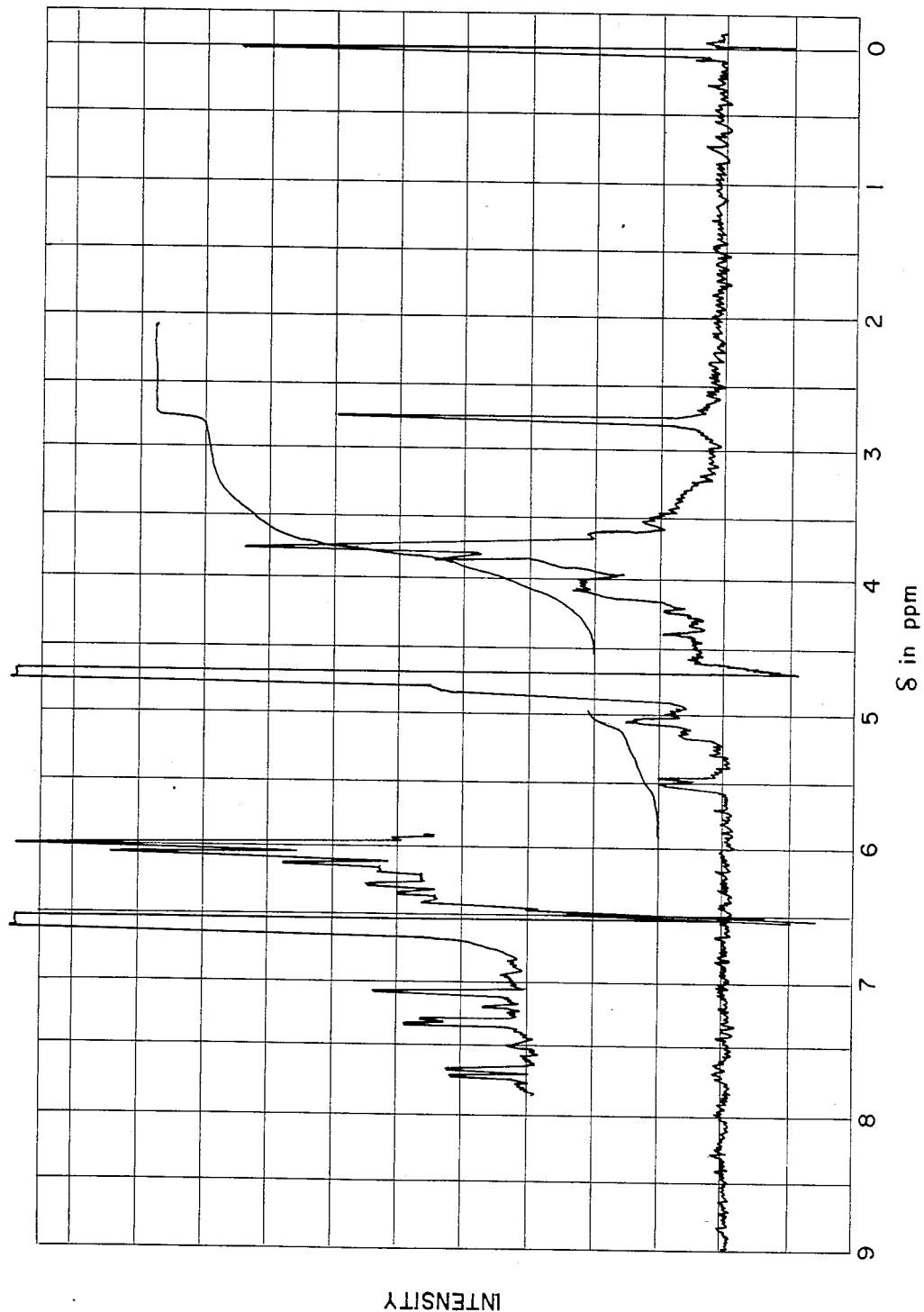
FIG. 3—$^1$H-NMR spectrum of boholmycin hydrochloride at 60 MHz, in $D_2O$ at PD 5.0.

The dihydrochloride salt of boholmycin is characterized by physico-chemical properties as set forth in Table 1 below. In this table the $^{13}$C-NMR spectrum of boholmycin dihydrochloride is that depicted in FIG. 1. The IR spectrum of boholmycin dihydrochloride in KBr is depicted in FIG. 2 and the $^1$H-NMR spectrum of boholmycin dihydrochloride is depicted in FIG. 3.

TABLE 1

| | |
|---|---|
| Nature | white amorphous powder |
| M.p. | 214–219° C. (dec.) |
| $[\alpha]_D^{28}$ | +52° (c 0.5, $H_2O$) |
| Elemental analysis | |
| Calcd. for | $C_{27}H_{48}N_4O_{21}.2HCl.4H_2O$ |
| | C 35.65, H 6.43, N 6.16, Cl 7.80 |
| Found | C 35.44, H 6.00, N 5.96, Cl 8.13 |
| Mass spectrum (FD-MS) | m/z 787 (M + Na), 765 (M + H) |
| UV | no absorption above 210 nm |
| $^{13}$C—NMR in ppm (multiplicity): | |
| 31.7 (q), 56.2 (d), 61.3 (t), 61.4 (d), 61.8 (t), 62.4 (t) | |
| 64.1 (d), 68.0 (d), 69.0 (d), 70.6 (d), 71.4 (d), 71.7 (d) | |
| 71.9 (d), 72.4 (d), 74.2 (d), 74.4 (d), 76.3 (d), 77.3 (d) | |
| 77.7 (d), 81.6 (d), 92.9 (d), 100.9 (d), 102.6 (d), | |
| 158.4 (s), 159.2 (s) | |

Boholmycin dihydrochloride displays no UV absorption maximum above 210 nm. The molecular formula has been assigned as $C_{27}H_{48}N_4O_{21}$ based on the elemental analysis of its hydrochloride and field-desorption mass spectrometry (M+H:m/z 765). The $^{13}$C-NMR spectrum indicates 25 signals with two of them having a double intensity. The IR spectrum (FIG. 2) shows strong absorption bands at 1720 and 1610 cm−1 which are attributable to O-carbamoyl group. The $^1$H-NMR spectrum (FIG. 3) includes three anomeric protons at δ:4.87 ppm (1H, s) 5.02 ppm (1H, d, J=1.6 Hz) and 5.46 ppm (1H, d, J=3.0 Hz), suggesting an oligosaccharide structure for boholmycin. Boholmycin is differentiated by thin layer chromatography (TLC) from three aminoglycoside antibiotics: streptomycin, glebomycin and myomycin B, which are related to boholmycin in some respects chemically or biologically. These results are displayed in Table 2.

TABLE 2

| | TLC Rf value (ninhydrin detection) | | | |
|---|---|---|---|---|
| System* | boholmycin | streptomycin | glebomycin | myomycin B |
| S-110 | 0.28 | 0.0 | 0.01 | 0.0 |
| S-120 | 0.21 | 0.15 | — | 0.04 |

TABLE 2-continued

| System* | TLC Rf value (ninhydrin detection) | | | |
|---|---|---|---|---|
| | boholmycin | streptomycin | glebomycin | myomycin B |
| S-124 | 0.44 | 0.41 | 0.51 | — |

*S-110: SiO$_2$, CHCl$_3$—MeOH—conc.NH$_4$OH—H$_2$O (1:4:2:1)
S-120: SiO$_2$, 95% EtOH—H$_2$O—AcOH—2N NH$_4$OH (79:21:5:10)
S-124: SiO$_2$, 10% AcONH$_4$—Acetone-conc.NH$_4$OH (9:10:1)

As previously indicated the boholmycin antibiotic herein is produced utilizing a culture of the microorganism *Streptomyces hygroscopicus* H617-25 ATCC No. 53240. This microorganism was isolated from a soil sample collected in Bohol Island in the Philippines.

Cultivation of the culture *Streptomyces hygroscopicus* H617-25 preferably takes place in aqueous nutrient media under submerged aerobic conditions with agitation at a temperature of 15° to 55° C., preferably 25° to 35° C. Nutrient media useful for cultivation include a source of assimilable carbon such as sugars, starches an glycerol; a source of assimilable nitrogen such as bacto-liver, cornsteep liquor, ammonium sulfate, casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results.

Preferably, the culture is inoculated into a medium comprising by weight from about 1% to about 5% source of assimilable carbon, from about 1% to about 5% source of assimilable nitrogen, from about 0.1% to about 2% of calcium source and from about 0.1% to about 1% NaCl, and sterile water.

Very preferably, the culture is inoculated from a slant into a medium comprisigg by weight from about 1% to about 5% glycerol, from about 1% to about 5% bacto-liver, from about 0.1% to about 2% (NH$_4$)$_2$SO$_4$, from about 1% to about 5% cornsteep liquor, from about 0.1% to about 2% calcium source (very preferably CaCO$_3$), from about 0.1% to about 1% NaCl, and sterile water.

If excessive foaming is encountered during fermentation, antifoam agents such as vegetable oils or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 250 cycles per minute whereas a fermentor is usually run at 200 to 300 revolutions per minute. Aseptic conditions must, of course, be maintained through the transfer of the organism and throughout its growth.

Inoculum for the preparation of the antibiotic according to this invention may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum in submerged inoculum tanks will usually be at the most favorable period in 1½ to 3 days.

The progress of antibiotic production during fermentation and the bioactivity of the fermentation broth can be monitored by biological assay of the broth employing a sensitive strain of *Staphylococcus aureus, Bacillus subtilis* or *Klebsiella pneumoniae. S. aureus* 209P, *B. subtilis* PCI-219 and *K. pneumoniae* No. 126 are suitable strains for this purpose. Standard paper disc assay technique is employed in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The Merck silica gel 60 F 254 chromatograms are developed with chloroform/methanol/conc. ammonia/water (1:4:2:1) or 95% ethanol/water/acetic acid/2N ammonia (79:21:5:10). The antibiotic compound is visualized by spraying with ninhydrin or anthrone reagent and heating the TLC plate at 80° C. The antibiotic will appear as a spot. The plate can also be overlayed with agar seeded with eithrr *S. aureus* or *B. subtilis* and incubated at 37° C. for 16 hours to visualize the antibiotic.

The antibiotic produced by fermentation of *Streptomyces hygroscopicus* H617-25 ATCC No. 53240 may be separated and recovered by using a weakly acidic ion exchange resin such as Amberlite IRC-50.

As previously recited the antibiotic producing microorganism strain, *Streptomyces hygroscopicus* H617-25, of the present invention was isolated from a soil sample collected in Bohol Island, Philippines. The determination of its genus and species was based upon its morphological, cultural and physiological characteristics, as well as the pattern of carbohydrate utilization of strain H617-25 which indicated that it belongs to the genus Streptomyces. According to the descriptions in *Bergey's Manual of Determinative Bacteriology*, 8th edition, pp. 748–829 (1974), strain H617-25 resembles the species group, Spirales, gray series, non-chromogenic, and smooth spore surface, which includes 65 species and 7 subspecies. Hygroscopic change of the aerial mycelium (blackening and moistening) is an additional important property of strain H617-25. Based on the descriptions in the *Bergey's Manual* and the study of Dietz in *Actinomycetes: The Boundary Microorganisms*, pp. 183–191 (1976), strain H617-25 was concluded to belong to the species, *Streptomyces hygroscopicus*.

The morphological observations of *Streptomyces hygroscopicus* H617-25 can be summarized as follows. It forms aerial and substrate mycelia with abundant sporulation, and the color of the aerial mycelium is white or pale orange yellow, which later turns to brownish shade of gray. This strain is gram-positive and forms coiled spore-chains on monopodially branched aerial sporophores. Tightly coiled spore-chain is often formed. These spore-chains contain 10 to 50 arthrospores in a chain. The spores are short-cylindrical, 0.6–0.8×0.8–1.2 μm in size, and have rugose or smooth surface. A hygroscopic change on the aerial mycelium occurs often in some agar media such as ISP No. 4 and No. 5.

*Streptomyces hygroscopicus* H617-25 grows well and forms mycelium in both nutritionally rich organic media and chemically defined agar media except for ISP No. 3 and No. 6 media. This microorganism does not produce melanoid pigment in tryptone-yeast extract broth (ISP No. 1) and peptone-yeast extract-iron agar (ISP No. 6) but produces weakly in tyrosine agar (ISP No. 7). Tyrosinase reaction is negative. It grows on agar medium containing NaCl at 6% but not at 8%. Whorl sporophore, motile spore and sporangium were not observed in any of the media examined.

The new culture *Streptomyces hygroscopicus* H617-25 was submitted on Aug. 7, 1985, to the American Type Culture Collection, Rockville, Md., and given the designation *Streptomyces hygroscopicus* H617-25 ATCC No. 53240. The permanency of the deposit of this culture at The American Type Culture Collection at Rockville, Md., and ready accessibility thereto by the public are afforded throughout the effective life of the patent in the event the patent is granted. Access to the culture is available during pendency of the application under 37 C.F.R. 1.14 and 35 U.S.C. 112. All restrictions on the availability to the public of the culture deposited will be irrevocably removed upon granting of the patent.

The pharmaceutically acceptable salts of the invention are those in which the anion does not contribute significantly to toxicity of the salt; these are typically acid additional salts.

For purposes of forming salt form of the antibiotics herein, there may be mentioned pharmaceutically acceptable acids such as hydrochloric and other hydrohalic acids, sulphuric, phosphoric, nitric, aliphatic, alicyclic, aromatic or heterocyclic carboxylic acids or sulphonic acids, such as formic, acetic, propionic, succinic, glycolic, lactic, malic, tartaric, citric, ascorbic, maleic, hydroxymaleic or pyruvic, fumaric, benzoic, p-aminobenzoic, anthranilic, p-hydroxy-benzoic, salicylic, or p-aminosalicylic, methanesulphonic, ethanesulphonic, hydroxyethanesulphonic, ethylenesulphonic, halogenobenzenesulphonic acid, toluenesulphonic acid, naphthalenesulphonic acid or sulphanilic acid. Hydrated salt derivatives may also be utilized in the instant invention.

Conventional methods are used to prepare the salts. Thus, admixture of the free base with the selected acid in an inert solvent such as water, ethyl acetate, methanol, dimethylformamide and the like with salt isolation by conventional concentration or crystallization techniques are employed. The acid salts are readily converted to free base form from acid salt form utilizing ion exchange resins which are known in the art.

The preferred salt of the instant antibiotic is boholmycin dihydrochloride tetrahydrate (boholmycin.2HCl.4H$_2$O).

The antibiotics of the instant invention display broad antibacterial activity against Gram-positive, Gram-negative and acid-fast bacteria including aminoglycoside resistant strains and are effective in vitro and in vivo in mammals. This antibacterial activity is displyyed in the examples which follow.

As previously indicated the antibiotics herein are useful in controlling antibacterial infectioss and are preferably administered as compositions including a pharmaceutically acceptable carrier and such compositions constitute a part of the invention. The antibiotics herein and pharmaceutical compositions containing them can be administered orally and parenterally. Examples of parenteral administration are intramuscular, intravenous, intraperitoneal, rectal and subcutaneous administration.

In respect to pharmaceutical compositions containing the antibiotics herein carrier and other ingredients should be such as not to diminish the therapeutic effects of the antibiotic. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tabeets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredients in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed wtth an inert solid diluent such as calcium carbonate, calcium phosphate and kaolin. The injectable compositions are formulated as known in the art and may contain appropriate dispersing or wetting agents and suspending agents identical or similar to those mentioned above.

EXAMPLE 1

Preparation of Boholmycin

A well-grown agar slant of *Streptomyces hygroscopicus* strain No. H617-25, was used to inoculate a vegetative medium consisting of 3% glycerol, 1% bacto-liver, 0.5% cornsteep liquor, 0.1% (NH$_4$)$_2$SO$_4$, 0.3% NaCl and 0.6% CaCO$_3$, the pH being adjusted to 7.0 before sterilization. The vegetative medium was incubated at 28° C. for 4 days on a rotary shaker (250 rpm) and 4 ml of the growth was transferred into a 500-ml Erlenmeyer flask containing 100 ml of production medium having the same composition as the vegetative medium. The fermentation was carried out at 28° C. with shaking on a rotary shaker. The antibiotic activity in the fermentation broth was determined by the paper-disc agar diffusion method using *Bacillus subtilis* PCI 219 as the test organism. A maximal antibiotic potency of approximately 500 mcg/ml was obtained after 4 to 5 days fermentation. The fermentation was also carried out in stir-jar fermentors. A 500-ml portion of the seed culture from flask fermentation was inoculated to 12 liters of the production medium in a 20-liter jar fermentor which was run at 28° C. with agitation at 250 rpm and aeration at 10 liters per minute. Antibiotic production reached a maximum of 300 mcg/ml after about 90 hours fermentation.

EXAMPLE 2

Isolation and Recovery of Boholmycin Dihydrochloride Tetrahydrate

The harvested broth (47 L, 300 mcg/ml) from the product of Example 1 was centrifuged using a Sharpless centrifuge (Kokusan No. 4A). The clarified fermentation liquor was adjusted to pH 7.0 and stirred with Amberlite IRC-50 (6L, 60% NH$_4$+) to adsorb the antibiotic activity. After being washed with water, the resin was eluted batchwisely with 0.5N NH$_4$OH (10L×2).

The eluates were pooled and concentrated in vacuo to a small volume (300 ml) which was diluted with an equal volume of methanol and added into acetone (9 L) to precipitate crude boholmycin (30.1 g).

The crude solid was dissolved in 100 ml of water and applied on a column of CM-Sephadex C-25 ($NH_4^+$ form, 2.4L). The column was eluted with a linear gradient prepared by water and 1.0M $NH_4Cl$ solution (4 L each). The eluates were collected in 30 ml fractions with an activity peak observed at fraction Nos. 221–240. The combined active fractions were loaded on a column of Sephadex LH-20 (8.4 L) which was preequilibrated with 50% aqueous methanol. The column was developed with the same solvent and the elution monitored by TLC (solvent system, $CHCl_3$—MeOH—conc.$NH_4OH$—$H_2O$=1:4:2:1) and bioassay (*B. subtilis* PCI 219). The fractions containing boholmycin were pooled, concentrated in vacuo and lyophilized to afford white powder of boholmycin hydrochloride (13 g).

EXAMPLE 3

In Vitro Antibacterial Activity of Boholmycin Hydrochloride

The minimum inhibitory concentration (MIC) of boholmycin dihydrochloride tetrahydrate was determined by a serial agar dilution method in comparison with sorbistin $A_1$, streptomycin and kanamycin. Nutrient agar (Difco) was used for all bacteria except for strains of Mycobacterium which were tested in No. 1001 agar. The results are shown in Table 3 wherein the term "boholmycin" is used for short in referring to boholmycin dihydrochloride tetrahydrate. As shown in Table 3, the antibacterial activity of boholmycin was comparable to that of sorbistin $A_1$ but generally weaker than that of streptomycin or kanamycin. However, boholmycin dihydrochloride tetrahydrate was as active against kanamycin and streptomycin-resistant organisms as against the sensitive ones.

Boholmycin dihydrochloride tetrahydrate was tested in comparison with streptomycin, glebomycin, myomycin B and kanamycin in respect to stimulating growth of *E. coli* D64 and in respect to inhibiting growth of *B. subtilis* PCI-219. The results are shown in Table 4 wherein the term "boholmycin" is used for short in referring to boholmycin dihydrochloride tetrahydrate. As shown in Table 4 boholmycin dihydrochloride tetrahydrate, like streptomycin-group of antibiotics, induced the growth of a streptomycin-dependent strain of *E. coli* D64. Myomycin B was also found to stimulate the growth of this organism.

TABLE 3

| Test organisms | Test* medium | MIC (mcg/ml) Boholmycin | sorbistin $A_1$ | streptomycin | kanamycin |
|---|---|---|---|---|---|
| *S. aureus* 209P | A | 200 | 50 | 1.6 | 0.8 |
| *S. aureus* Smith | A | 200 | 50 | 1.6 | 0.4 |
| *S. aureus* A20239** | A | >200 | 100 | >100 | >100 |
| *M. luteus* PCI-1001 | A | 200 | 50 | 3.1 | 6.3 |
| *M. flavus* D-12 | A | 100 | 12.5 | 0.8 | 1.6 |
| *B. subtilis* ATCC6633 | A | 50 | 50 | 0.8 | 0.2 |
| *B. anthracis* IID-115 | A | 25 | 50 | 0.4 | 0.4 |
| *E. coli* NIHJ | A | 50 | 25 | 1.6 | 0.8 |
| *E. coli* Juhl | A | 100 | 50 | 3.1 | 1.6 |
| *E. coli* K-12 | A | 25 | 25 | 1.6 | 0.8 |
| *E. coli* A20664** | A | 12.5 | 25 | >100 | >100 |
| *E. coli* JR35/c600** | A | 25 | 25 | >100 | >100 |
| *K. pneumoniae* D-11 | A | 6.3 | 6.3 | 0.4 | 0.4 |
| *K. pneumoniae* A9678 | A | 100 | 100 | 6.3 | 3.1 |
| *E. cloacae* A20364** | A | 50 | 50 | >100 | >100 |
| *E. cloacae* A21006** | A | 50 | 50 | >100 | >100 |
| *P. mirabilis* A9554 | A | 50 | 50 | 1.6 | 0.8 |
| *P. vulgaris* A9436 | A | 6.3 | 50 | 0.4 | 0.2 |
| *S. marcescens* A20019 | A | 100 | >200 | 25 | 1.5 |
| *S. marcescens* A22302** | A | 100 | 400 | >100 | 50 |
| *P. aeruginosa* A9930 | A | 100 | 12.5 | >100 | 12.5 |
| *P. aeruginosa* A9843A | A | 200 | 6.3 | >100 | 6.3 |
| *P. aeruginosa* A20601** | A | 12.5 | 3.1 | 3.1 | >100 |
| Mycobacterium 607 D87 | B | 25 | 50 | 0.4 | 0.2 |
| Mycobacterium 607 D46** | B | 25 | 100 | 0.4 | >100 |
| *Mycobacterium phlei* | B | 6.3 | 25 | 0.2 | 0.4 |
| *Mycobacterium ranae* | B | 25 | 50 | 0.4 | 0.2 |

*A: Nutrient agar (Difco), B: No. 1001 medium (3% glycerol, 0.3% sodium L-glutamate, 0.2% peptone, 0.31% $Na_2HPO_4.12H_2O$, 0.1% $KH_2PO_4$, 0.005% ammonium citrate, 0.001% $MgSO_4$, 1.5% agar)
**kanamycin resistant strain

TABLE 4

| Antibiotic | Conc*1 (mg/ml) | Growth zone*2 vs *E. coli* D64 (mm) | Inhibition zone vs*3 *B. subtilis* PCI-219 (mm) |
|---|---|---|---|
| Boholmycin | 40 | 18 (23)*4 | 33 |
|  | 10 | + (16) | 30 |
| Streptomycin | 0.25 | 17 (28) | 35 |
|  | 0.06 | + (14) | 32 |
| Glebomycin | 4 | 27 | 33 |
|  | 1 | 15 | 30 |
| Myomycin B | 1 | 17 (34) | 34 |
|  | 0.25 | + (28) | 29 |
| Kanamycin | 0.4 | — | 34 |
|  | 0.1 | — | 30 |

*1 8 mm paper disc containing 35 μl of test solution
*2 Incubation at 37° C. for 45 hours
*3 Incubation at 28° C. for 18 hours
*4 ( ) hazy growth zone

EXAMPLE 5

In Vivo Activity of Boholmycin Dihydrochloride Tetrahydrate

The in vivo efficacy of boholmycin dihydrochloride tetrahydrate was tested in mice against experimental infections produced by *S. aureus*, *E. coli* and *K. pneumoniae*. Mice were challenged with a multiple of the lethal doses of the pathogens in a 5% suspension of gastric mucin (American Laboratory, Omaha, Nebr.). Boholmycin dihydrochloride tetrahydrate was administered intramuscularly just before the bacterial challenge. The mice were observed for 5 days to determine the median protective dose ($PD_{50}$). Sorbistin $A_1$, streptomycin and kanamycin were comparatively tested as reference antibiotics. The results are presented in Table 5 wherein the term "boholmycin" is used for short in referring to boholmycin dihydrochloride tetrahydrate. As shown in Table 5, the boholmycin salt and sorbistin $A_1$ showed similar in vivo activity but were much less active than streptomycin and kanamycin.

TABLE 5

| | $PD_{50}$ (mg/kg, i.m.) | | | |
|---|---|---|---|---|
| Test organisms | boholmycin | sorbistin $A_1$ | streptomycin | kanamycin |
| *S. aureus* Smith | 75 | 50 | 1.9 | 1.1 |
| *E. coli* Juhl | 100 | 100 | 1.4 | 3.5 |
| *K. pneumoniae* D-11 | 65 | 75 | 0.85 | 1.1 |

Boholmycin dihydrochloride tetrahydrate did not show any toxic signs in mice up to a dose of 1,000 mg/kg by intravenous administration.

Other variations will be evident to those skilled in the art. Therefore, the scope of the invention is intended to be defined by the claims.

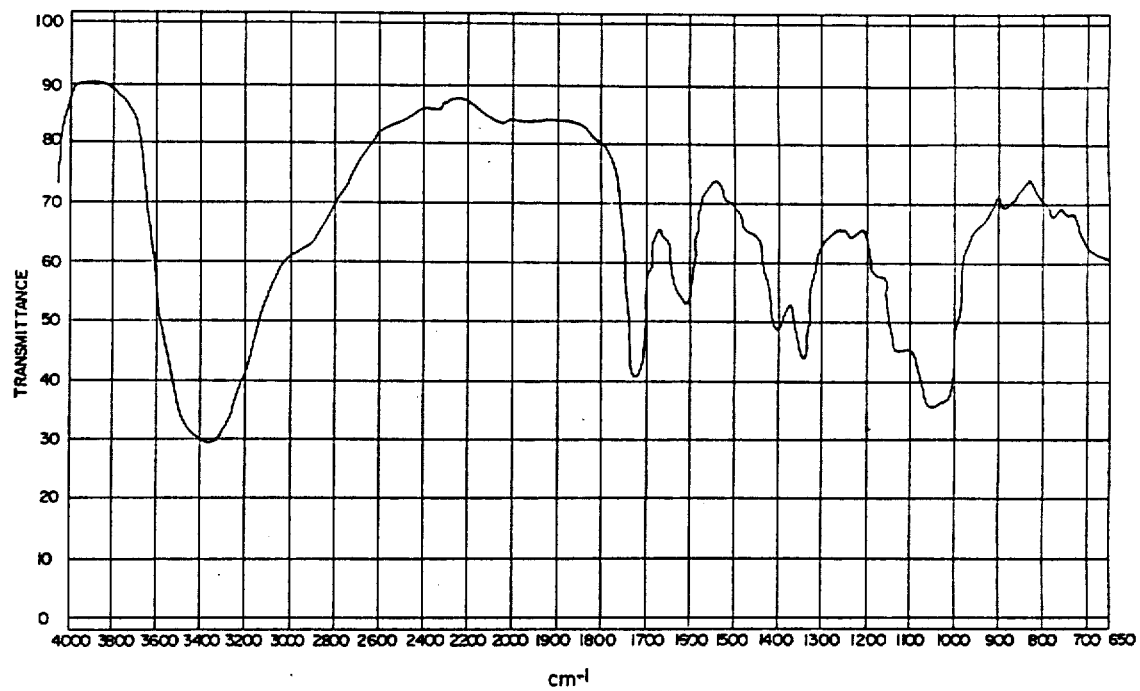

We claim:

1. A boholmycin compound represented by the structural formula:

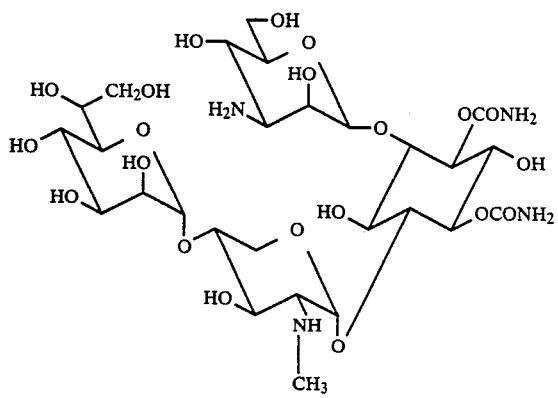

and its non-toxic pharmaceutically acceptable salts and hydrates.

2. The compound of claim 1 which is boholmycin dihydrochloride tetrahydrate.

3. A pharmaceutical composition for treatment of bacterial infections containing a therapeutically effective amount of the compound of claim 1 and a pharmaceutically acceptable carrier.

* * * * *

UNITED STATES PATENT AND TRADEMARK OFFICE
CERTIFICATE OF CORRECTION

PATENT NO. : 4,792,545

DATED : December 20, 1988

INVENTOR(S) : Kyoichiro Saitoh, Mitsuaki Tsunakawa, Masataka Konishi, and Takeo Miyaki It is certified that error appears in the above-identified patent and that said Letters Patent is hereby corrected as shown below:

Delete sheet 2 of 3 comprising Fig. 1A, Fig. 2 and Fig. 2A and insert Sheet 2 as shown on the attached sheet.

Signed and Sealed this

Twenty-sixth Day of December, 1989

*Attest:*

JEFFREY M. SAMUELS

*Attesting Officer*   *Acting Commissioner of Patents and Trademarks*

UNITED STATES PATENT AND TRADEMARK OFFICE
CERTIFICATE OF CORRECTION

PATENT NO. : 4,792,545

DATED : December 20, 1988

INVENTOR(S) : Kyoichiro Saitoh, Mitsuaki Tsunakawa, Masataka Konishi, and Takeo Miyaki It is certified that error appears in the above-identified patent and that said Letters Patent is hereby corrected as shown below: